United States Patent
Fuller et al.

(10) Patent No.: US 10,682,494 B2
(45) Date of Patent: Jun. 16, 2020

(54) GUIDE EXTENSION CATHETER

(71) Applicant: BOSTON SCIENTIFIC SCIMED, INC., Maple Grove, MN (US)

(72) Inventors: Jeffrey Steven Fuller, Brooklyn Park, MN (US); James M. Anderson, Corcoran, MN (US); John E. Uschold, North Branch, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 449 days.

(21) Appl. No.: 15/165,124

(22) Filed: May 26, 2016

(65) Prior Publication Data

US 2016/0346502 A1    Dec. 1, 2016

Related U.S. Application Data

(60) Provisional application No. 62/169,541, filed on Jun. 1, 2015.

(51) Int. Cl.
*A61M 25/00* (2006.01)
*A61M 25/01* (2006.01)
(Continued)

(52) U.S. Cl.
CPC ...... *A61M 25/008* (2013.01); *A61M 25/0009* (2013.01); *A61M 25/0069* (2013.01); *A61M 25/0108* (2013.01); *A61M 25/04* (2013.01); *A61M 2025/0175* (2013.01); *B29C 48/21* (2019.02); *B29K 2101/12* (2013.01);
(Continued)

(58) Field of Classification Search
CPC ............ A61M 25/008; A61M 25/0009; A61M 25/0069; A61M 25/0108; A61M 2025/0175; B29C 47/065; B29L 2031/7542
See application file for complete search history.

(56) References Cited

U.S. PATENT DOCUMENTS 5,238,004 A  8/1993 Sahatjian et al.
5,772,609 A  6/1998 Nguyen et al.
(Continued)

FOREIGN PATENT DOCUMENTS

CN  104602718 A  5/2015
CN  104812420 A  7/2015
(Continued)

*Primary Examiner* — Laura A Bouchelle
*Assistant Examiner* — Justin L Zamory
(74) *Attorney, Agent, or Firm* — Seager, Tufte & Wickhem, LLP

(57) ABSTRACT

Medical devices and methods for making and using medical devices are disclosed. An example medical device may include a guide extension catheter. The guide extension catheter may include a proximal member having a proximal end, a distal end, and a proximal diameter. The guide extension catheter may additionally include a collar member attached to the distal end of the proximal member, the collar member comprising a base portion and one or more ribs connected to the base portion and extending distally away from the base portion. In still some additional embodiments, the guide extension catheter may further include a distal sheath member attached to the collar member, the distal sheath member having a distal diameter larger than the proximal diameter.

20 Claims, 7 Drawing Sheets

(51) Int. Cl.
*A61M 25/04* (2006.01)
*B29K 101/12* (2006.01)
*B29L 31/00* (2006.01)
*B29C 48/21* (2019.01)

(52) U.S. Cl.
CPC ............... *B29K 2995/0011* (2013.01); *B29L 2031/7542* (2013.01)

(56) References Cited

U.S. PATENT DOCUMENTS

| | | | |
|---|---|---|---|
| 5,922,019 A | 7/1999 | Hankh et al. | |
| 6,139,510 A | 10/2000 | Palermo | |
| 6,508,803 B1 | 1/2003 | Horikawa et al. | |
| 2008/0188928 A1* | 8/2008 | Salahieh ........... | A61M 25/0054 623/2.11 |
| 2011/0160763 A1 | 6/2011 | Ferrera et al. | |
| 2013/0144328 A1* | 6/2013 | Weber ................ | A61F 2/958 606/200 |
| 2014/0012281 A1* | 1/2014 | Wang ................ | A61M 25/0023 606/108 |
| 2014/0052097 A1 | 2/2014 | Petersen et al. | |
| 2014/0081243 A1 | 3/2014 | Zhou et al. | |

FOREIGN PATENT DOCUMENTS

| | | |
|---|---|---|
| EP | 1639951 A1 | 3/2006 |
| EP | 1534178 B1 | 10/2007 |
| JP | H-09168597 A | 6/1997 |
| JP | 2006087643 A | 4/2006 |
| JP | 2014147458 A | 8/2014 |
| WO | 2007035471 A2 | 3/2007 |
| WO | 2014011677 A1 | 1/2014 |
| WO | 2014028898 A2 | 2/2014 |

\* cited by examiner

GUIDE EXTENSION CATHETER

CROSS REFERENCE TO RELATED APPLICATIONS

This application claims the benefit of U.S. Provisional Patent Application Ser. No. 62/169,541 filed on Jun. 1, 2015, the disclosures of each incorporated herein by reference.

TECHNICAL FIELD

The present disclosure pertains to medical devices, and methods for manufacturing medical devices. More particularly, the present disclosure pertains to elongated intracorporeal medical devices including a guide extension catheter.

BACKGROUND

A wide variety of intracorporeal medical devices have been developed for medical use, for example, intravascular use. Some of these devices include guidewires, is catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. In one example, a guide extension catheter may comprise a proximal member having a proximal end, a distal end, and a proximal diameter. The guide extension catheter may additionally comprise a collar member attached to the distal end of the proximal member, the collar member comprising a base portion and one or more ribs connected to the base portion and extending distally away from the base portion. Additionally, in some examples the guide extension catheter may include a distal sheath member attached to the collar member, the distal sheath member having a distal diameter larger than the proximal diameter.

Additionally, or alternatively, in the above example, each of the one or more ribs may be connected to the base portion at an angle of between about 15 degrees and about 75 degrees.

Additionally, or alternatively, in the above example, the ribs may extend from the base portion to the distal end of the collar.

Additionally, or alternatively, in any of the above examples, each of the one or more ribs may be connected to the base portion at an angle of between about 30 degrees and about 60 degrees.

Additionally, or alternatively, in any of the above examples, each of the one or more ribs may be connected to the base portion at an angle of about 45 degrees.

Additionally, or alternatively, in any of the above examples, the one or more ribs may comprise between two ribs and ten ribs.

Additionally, or alternatively, in any of the above examples, the one or more ribs may comprise between four ribs and seven ribs.

Additionally, or alternatively, in any of the above examples, the one or more ribs may comprise five ribs.

Additionally, or alternatively, in any of the above examples, the ribs extend away from the base portion in a twisting manner.

Additionally, or alternatively, in any of the above examples, the ribs may extend away from the base portion in a helical manner.

Additionally, or alternatively, in any of the above examples, the ribs may extend away from the base portion in a sinusoidal manner.

Additionally, or alternatively, in any of the above examples, the ribs may extend away from the base portion in an undulating manner.

Additionally, or alternatively, in any of the above examples, each of the one or more ribs may extend away from the base portion a same distance.

Additionally, or alternatively, in any of the above examples, the one or more ribs may not vary in cross-sectional area as they extend distally away from the base portion.

Additionally, or alternatively, in any of the above examples, the one or more ribs may vary in cross-sectional area as they extend distally away from the base portion.

Additionally, or alternatively, in any of the above examples, the one or more ribs may taper in cross-sectional area as they extend distally away from the base portion.

Additionally, or alternatively, in any of the above examples, the collar member may comprise a hollow tube with portions of the tube removed to form the ribs.

Additionally, or alternatively, in any of the above examples, the collar member may comprise a slot, and wherein the distal end of the proximal member may be bonded to the collar member in the slot.

In another example, a guide extension catheter may comprise a proximal member having a proximal end, a distal end, and a proximal diameter. In some of these examples, the guide extension catheter may further comprise a hollow tube extending along a longitudinal axis and attached to the distal end of the proximal member, the hollow tube defining one or more channels extending along at least a portion of the hollow tube and a distal sheath member attached to the hollow tube, the distal sheath member having a distal diameter greater than the proximal diameter. Additionally, in some examples, the is channels may be angled with respect to the longitudinal axis of the hollow tube.

Additionally, or alternatively, in the above example, the channels may extend from the base portion to the distal end of the collar.

Additionally, or alternatively, in the above example, the one or more channels may be angled between about 15 degrees and 75 degrees with respect to the longitudinal axis.

Additionally, or alternatively, in any of the above examples, the one or more channels may be angled between about 30 degrees and 60 degrees with respect to the longitudinal axis.

Additionally, or alternatively, in any of the above examples, the one or more channels may comprise between two channels and ten channels.

Additionally, or alternatively, in any of the above examples, the one or more channels may comprise between four and seven channels.

Additionally, or alternatively, in any of the above examples, the hollow tube may define the one or more channels such that each of the one or more channels has an open end and a closed end.

In yet another example, a guide extension catheter may comprise a proximal member having a proximal end, a distal end, and a proximal diameter. In some of these examples, the guide extension catheter may further comprise a collar member attached to the proximal member, the collar member having a proximal end and distal end and comprising a base portion and a distally extending portion, and a distal sheath member attached to the distally extending portion, the distal sheath member having a distal diameter greater than the proximal diameter. Additionally, in some examples, the collar member may have a cross-sectional surface area that varies less than about 33% through the distally extending portion.

Additionally, or alternatively, in the above example, the collar member may have a cross-sectional surface area that varies less than about 10% along the distally extending portion.

Additionally, or alternatively, in any of the above examples, the distally extending portion may comprise ribs connected to the base portion and extending distally away is from the base portion.

Additionally, or alternatively, in any of the above examples, the ribs may extend distally away from the base portion in a helically twisting manner.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
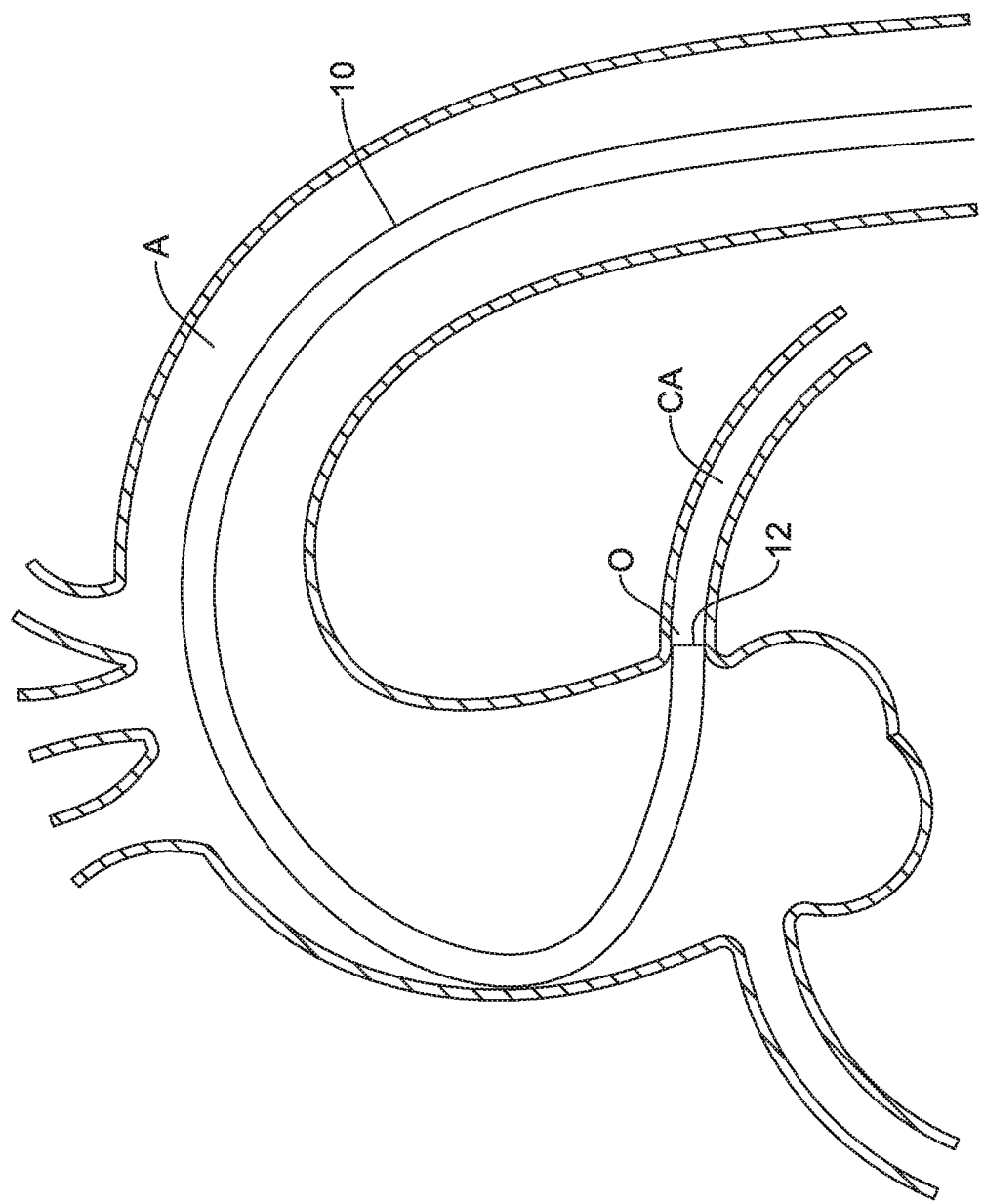
FIG. 1 is a plan view illustrating an example guide catheter advanced through the aorta to the ostium of a coronary artery.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to to limit the scope of the invention.

Minimally-invasive cardiac interventions such as percutaneous transluminal coronary angioplasty are widely utilized throughout the world. These procedures may include the use of a guide catheter. For example, a guide catheter 10 may be advanced through a blood vessel such as the aorta A to a position adjacent to the ostium O of a is (e.g., left and/or right) coronary artery CA as illustrated in FIG. 1. When so positioned, a treatment catheter (e.g., balloon catheter, stent delivery system, etc.) may be advanced through guide catheter 10 and into the coronary artery CA to a target location where the treatment catheter may be used to perform the appropriate cardiac intervention.

In order for the treatment catheter to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Figure 2:
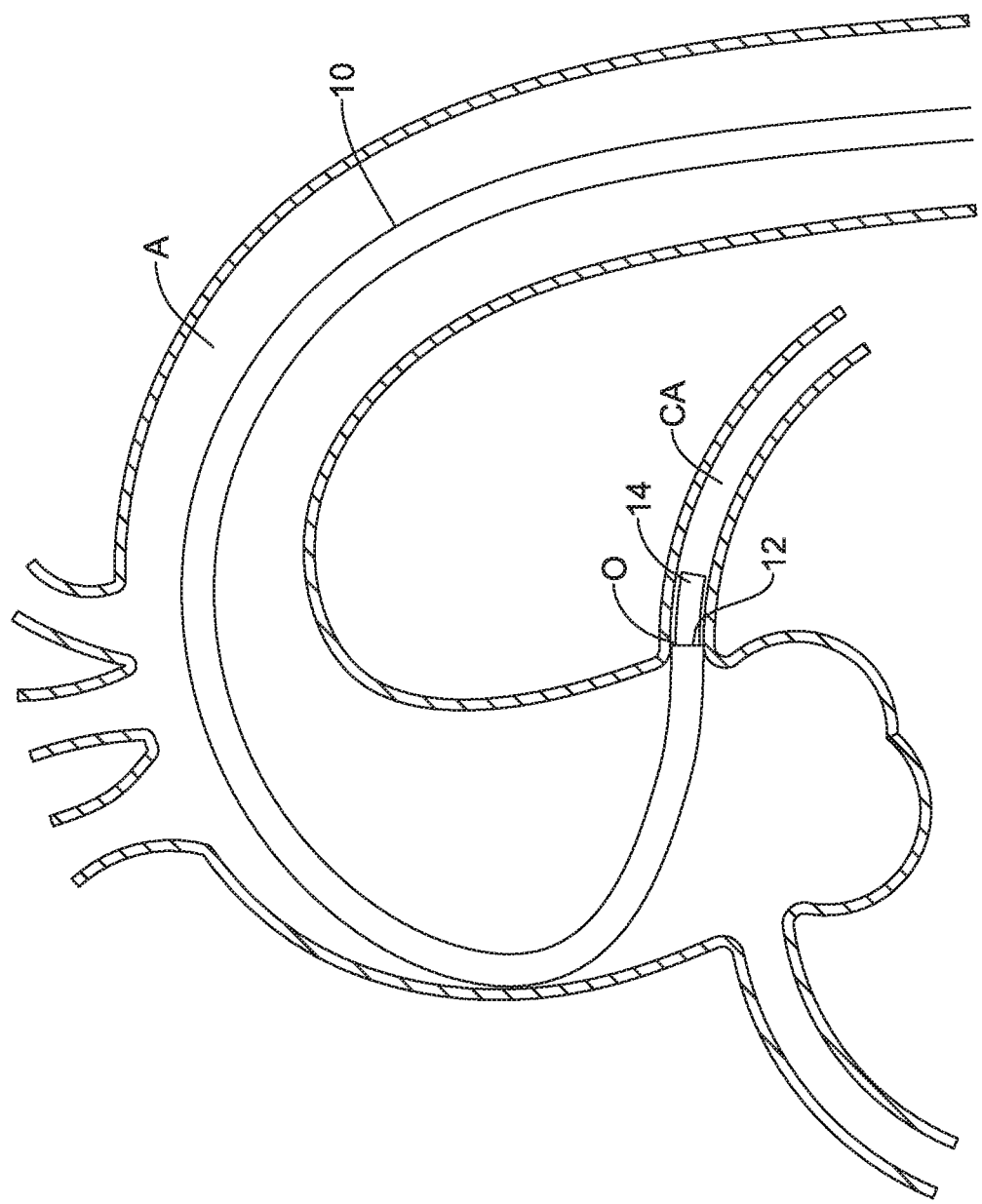
FIG. 2 is a plan view illustrating an example guide extension catheter used in conjunction with a guide catheter.

Disclosed herein are medical devices and methods for making and using medical devices that may improve access to the coronary arteries CA. For example, FIG. 2 illustrates a guide extension catheter 14 extending through guide catheter 10 and beyond distal end 12 of guide catheter 10 into the coronary artery CA. Because, for example, guide extension catheter 14 may extend beyond distal end 12 of guide catheter 10, guide extension catheter 14 may extend beyond the ostium O of the coronary artery CA and into a portion of the coronary artery CA. By extending beyond the ostium O, the extension catheter 14 may stabilize the positioning of guide catheter 10 and allow for improved access to the coronary artery CA for a number of cardiac interventions.

Figure 3:
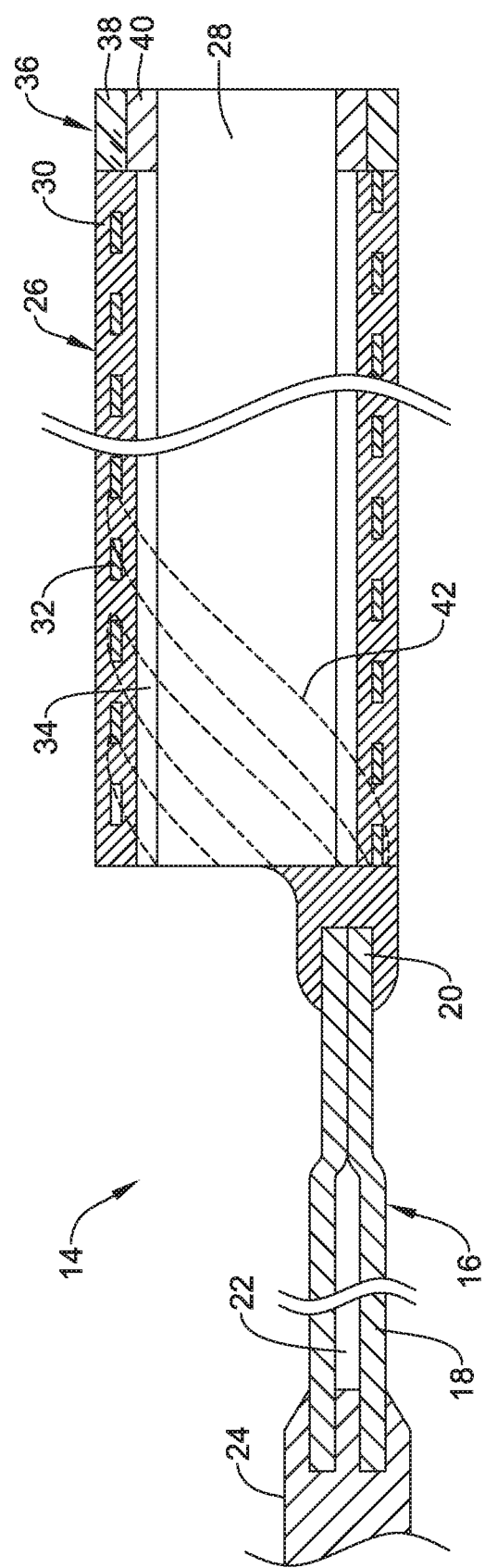
FIG. 3 is a cross-sectional side view of an example guide extension catheter.

FIG. 3 is a cross-sectional side view of guide extension catheter 14. Here it can be seen that guide extension catheter 14 may include a shaft or member 16. Member 16 may include a proximal portion 18 and a distal or ribbon portion 20. Proximal portion 18 may have a lumen 22 defined therein. In some embodiments, lumen 22 extends along the entire length of proximal portion 18. In other embodiments, lumen 22 extends along only a portion of the length of proximal portion 18. In still other embodiments, member 16 may be a hypotube and have a lumen extending along the entire length of member 16. In addition, proximal portion 18 may include both proximal and distal openings (e.g., is positioned at the proximal and distal end of proximal portion 18) such that lumen 22 is "open" on both ends. Alternatively, one or both of the ends of proximal portion 18 may be closed or otherwise sealed. For example, the distal end of proximal portion 18 may be closed. In some of these and in other embodiments, proximal portion 18 may have an opening or port (not shown) formed in the wall of proximal portion 18 and spaced from the proximal and/or distal end of proximal portion 18. The port may or may not be in fluid communication with lumen 22. A hub 24 may be attached to proximal portion 18.

A distal sheath 26 may be attached to member 16. Sheath 26 may have a lumen 28 formed therein. In general, lumen 28 (and/or the inner diameter of distal sheath 26) may be larger than lumen 22 (and/or the inner diameter of proximal portion 18) and may be larger than the outer diameter of member 16. As used herein, the term diameter may refer to a line from one side of something to a second side of the something, wherein the line passes through a center point of the something. Illustratively, the something may be a cross-sectional shape of a square, a circle, a triangle, an oval, a rectangle, or other shape. With respect to proximal member 16 and/or distal sheath 26 that may not have a circular cross-sectional shape, the diameter of such shapes may be the largest cross-sectional dimension of proximal member 16 or distal sheath 26 taken from a cross-section transverse to a longitudinal dimension (e.g., to a direction of a longitudinal axis. Accordingly, lumen 28 may be sufficiently large so as to allow a therapeutic catheter (e.g., balloon catheter, stent delivery system, etc.) to pass therethrough. For example, when guide extension catheter 14 is positioned within guide catheter 10, the therapeutic catheter may extend within guide catheter 10 alongside member 16 and through lumen 28 of distal sheath 26.

Distal sheath 26 may include a body portion 30. In at least some embodiments, body portion 30 may include one or more polymers including any of those disclosed herein. This may include the use of polymers with a differing durometer along the length of body portion 30. For example, a more proximal section of body portion 30 may include a polymer with a higher durometer and a more distal section of body portion 30 may include a polymer with a lower durometer. Portions of all of the length of body portion 30 may be loaded with or otherwise include a radiopaque material. Body portion 30 may also include a reinforcement member 32. The form of reinforcement member 32 is may vary. For example, reinforcement member 32 may include a braid, coil, mesh, rings, segments, fibers or interstitial arrays of fibers, or the like.

An inner liner or layer 34 may be disposed along an inner surface of body portion 30. The form of liner 34 may vary. For example, liner 34 may be a lubricious liner or otherwise include a lubricious material such as polytetrafluoroethylene. A tip member 36 may be attached to body portion 30, for example at a distal end of body portion 30. In some embodiments, tip member 36 may be a single layer of material. Alternatively, tip member 36 may include an outer layer 38 and an inner layer 40. Outer layer 38 and inner layer 40 may be formed from the same material. In some of these embodiments, outer layer 38 and inner layer 40 may include the same polymeric material and each be loaded with the same or different radiopaque materials. For example, inner layer 40 may include a polyether block amide loaded with approximately 75-95% (e.g., about 90%) by weight tungsten and outer layer 38 may include a polyether block amide loaded with approximately 30-50% (e.g., 40%) by weight bismuth subcarbonate. These are just examples. In other embodiments, outer layer 38 and inner layer 40 may be made from different materials.

Distal sheath 26 may be attached to ribbon portion 20 of member 16. The arrangement and/or configuration of the attachment between ribbon portion 20 and distal sheath 26 may vary. For example, distal sheath 26 may have an opening or lumen formed in tube wall thereof and ribbon portion 20 may be disposed within the opening. This may include necking, skiving, or pinching down ribbon portion 20 and inserting the necked down portion into the opening. In some embodiments, inserting ribbon portion 20 into the opening may secure member 16 to distal sheath 26 via a mechanical bond. In some of these and in other embodiments, additional and/or alternative bonding may be utilized including those bonding mechanisms commonly used for medical devices. Some example bonding mechanisms include adhesive bonding, welding, thermal bonding, brazing, metallurgical stamping, pressing etc. Other attachment mechanisms are also contemplated for attaching member 16 to distal sheath 26 including direct bonding (e.g., adhesive bonding, thermal bonding, welding, brazing, injection molding, 3D printing and bonding, overmolding, casting, sintering polymer/metal composites, etc.), bonding that is is facilitated by a third component such as a metal or polymer collar 42 that may be bonded between the ribbon portion 20 and distal sheath 26.

Guide extension catheter 14 may also include a number of coatings that may, for example, reduce friction. For example, proximal member 16 may have an inner and/or outer coating that includes a hydrophilic polymer that may reduce friction during tracking. An example coating may include BAYER CL-100, BIOSLIDE, NG-HPC, SLIP COAT, MDX, ZGLIDE, or the like. These are just examples. Other materials are contemplated including those disclosed herein.

Figure 4:
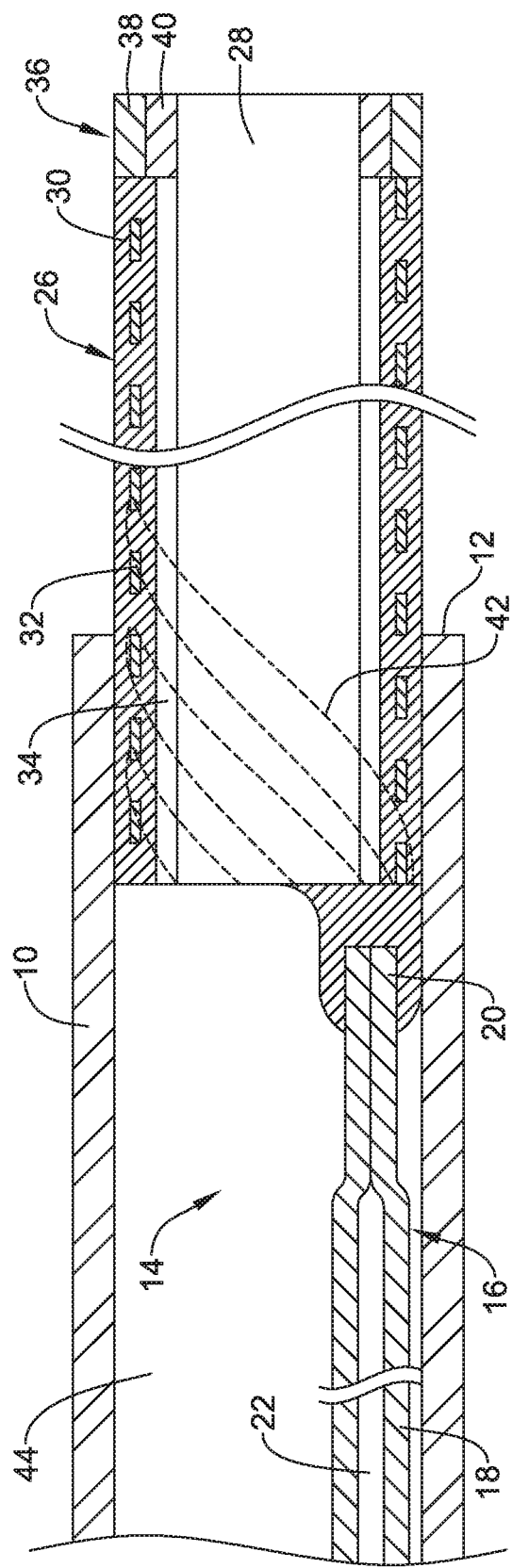
FIG. 4 is a cross-sectional side view of the example guide extension catheter and an example guide catheter.

FIG. 4 illustrates guide extension catheter 14 disposed within guide catheter 10 (e.g., disposed within a lumen 44 defined within guide catheter 10). As shown, distal sheath 26 may be arranged to extend distally out from distal end 12 of guide catheter 10. When so arranged, distal sheath 26 may engage the ostium O and/or extend within a portion of the coronary artery CA to help maintain the position of guide catheter 10 and improve access to the coronary artery CA. Member 16 may be designed to be sufficiently small (while still being sufficiently sized and configured for pushability) so as to take up relatively little space within the interior or lumen 44 of guide catheter 10. Accordingly, the use of guide extension catheter 14 allows for a therapeutic catheter or medical device to be advanced through guide catheter 10 in order to reach the desired target location for the intervention. In some embodiments, member 16 may contact the inner wall surface of guide catheter 10, which may provide even more space.

As discussed, some embodiments of guide extension catheter 14 may include collar 42 connected between member 16 and distal sheath 26, as illustrated in FIGS. 3 and 4. In some embodiments, collar 42 may be sized to work with a guide catheter 10 or guide extension catheter 14 that have sizes between about 4 French to about 9 French. However, in other embodiments, collar 42 may be sized differently to cooperate with guide catheters 10 and/or guide extension catheters 14 that are smaller than 4 French and larger than 9 French.

Figure 5A:
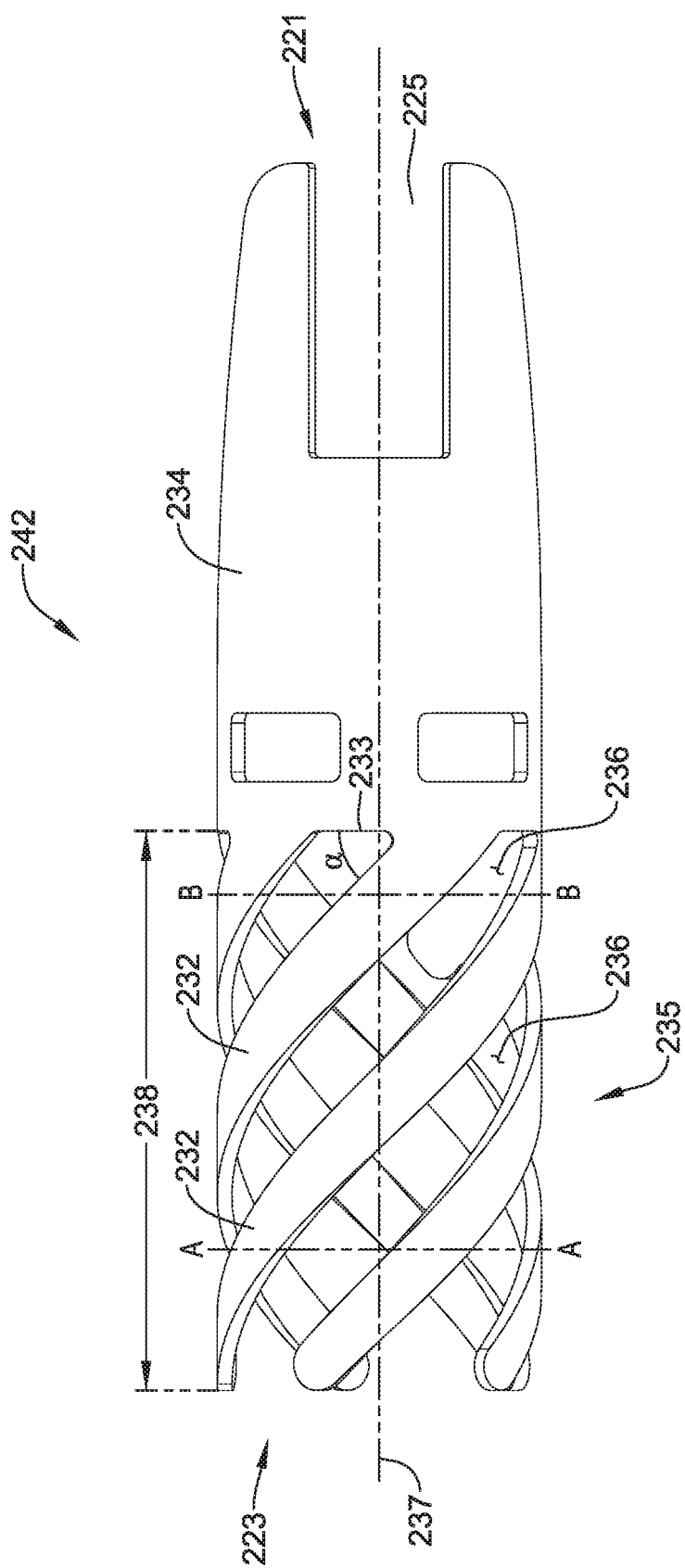
FIG. 5A is a top view of an example guide extension catheter collar.
Figure 5B:
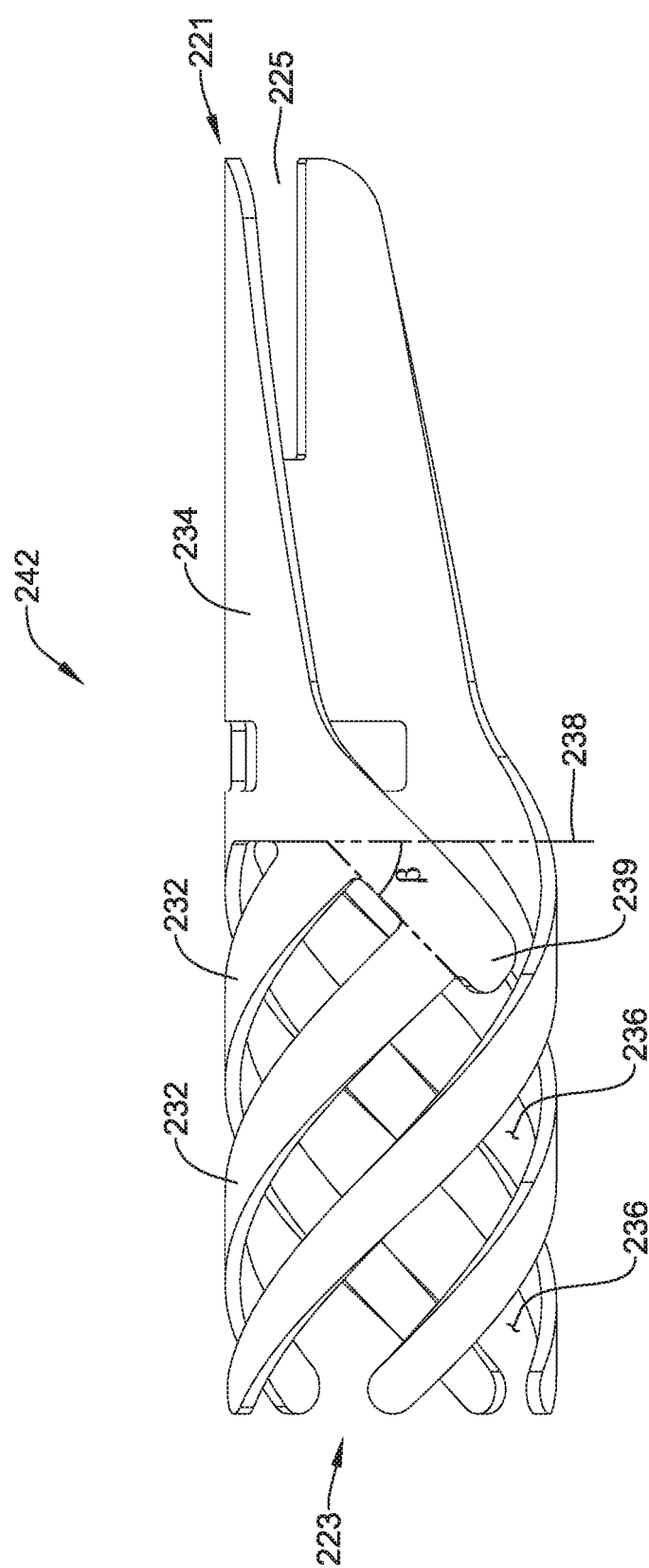
FIG. 5B is side view of an example guide extension catheter collar.

FIGS. 5A and 5B are different illustrative perspective views of an exemplary collar member 242 that may be used to facilitate bonding between a ribbon portion and a distal sheath of a guide extension catheter, such as ribbon portion 20 and distal sheath 26 of guide extension catheter 14 described with respect to FIGS. 3 and 4. FIG. 5A is depicts collar member 242 including proximal end 221 and distal end 223. Collar member 242 comprises base portion 234 and a distally extending portion 235. In some embodiments, distally extending portion 235 may comprise ribs 232 which extend distally away from base portion 234. As shown in FIG. 5A, ribs 232 may extend from base portion 234 all the way to distal end 223 of collar member 242. However, in other embodiments this does not need to be the case. One or more of ribs 232 may not extend all the way to distal end 232 of collar member 242. Additionally, ribs 232 are just one example of distally extending portion 235.

Collar member 242 may additionally include slot 225. To attach collar member 242 to a member, such as member 16 of FIGS. 3 and 4, a distal end of the member may be inserted into slot 225 and may be bonded to collar member 242 by bonding mechanisms commonly used for medical devices. Some example bonding mechanisms include adhesive bonding, welding, thermal bonding, brazing, etc.

Distally extending portion 235 may be attached to a sheath, such as sheath 26 of FIGS. 3 and 4, in a similar manner to how proximal member 16 may be attached to collar member 242. In other embodiments, distally extending portion 235 may be inserted into one end of the sheath, and both the distally extending portion 235 and the sheath may be heated. This heat may cause the material of the sheath to melt and flow into and/or around distally extending portion 235. When the heat is removed, the melted material may solidify, thereby bonding the sheath to distally extending portion 235.

In embodiments where distally extending portion 235 comprises ribs 232, ribs 232 may extend distally away from base portion 234 at an angle α, which is defined as the angle between top of base portion 233 and rib 232. In the example of FIG. 5A, α is 45 degrees. However, in different embodiments, angle α may have any value between about 15 degrees and about 75 degrees. In some more specific embodiments, angle α may have any value between about 30 degrees and about 60 degrees.

Although FIGS. 5A and 5B depict collar member 242 having five ribs 232, in other embodiments, collar member 242 may have a different number of ribs 232. For instance, in different embodiments, collar member 242 may have between about one rib 232 and about ten ribs 232. In more specific embodiments, collar member 242 may have between about four ribs 232 and about seven ribs 232. Additionally, in at least some is embodiments, ribs 232 may extend distally away from base portion 234 in a twisting manner. As one example, ribs 232 may have a helical twist and extend distally away from base portion 234 in a helical manner. Although shown as extending in a generally clockwise helical manner when viewing collar member 242 from proximal end 221, in other embodiments, the helical twist may be counter-clockwise. In some of these embodiments, each of ribs 232 may extend helically around longitudinal axis 237 at least 90 degrees. In other embodiments, each of ribs 232 may extend helically around longitudinal axis 237 about 180 degrees, about 360 degrees, or anywhere between 90 degrees and 360 degrees. In still other embodiments, each of ribs 232 may helically twist around longitudinal axis 237 multiple times as ribs 232 extend distally from base portion 234.

In still other embodiments, ribs 232 may not extend distally away from base portion 234 in a twisting manner at all. For instance, ribs 232 may extend distally away from base portion 234 in a straight manner. In at least some embodiments, ribs 232 may have one or more connecting members disposed generally transverse to the direction of ribs 232, connecting ribs 232 together. The connecting members may simply be thin portions of collar member 242 left during the processing to form ribs 232. These connecting members may be relatively thin compared to the width of ribs 232. In some additional embodiments, ribs 232 may have a wavy or sinusoidal shape. For instance, ribs 232 may extend generally distally away from base portion 234 in a straight fashion, except ribs 232 may curve back and forth transversely to longitudinal axis 237. Or, in other embodiments, ribs 232 may undulate up and down in a manner parallel to longitudinal axis 237.

FIG. 5A additionally depicts ribs 232 extending away from base portion 234 a distance 238. In different embodiments, distance 238 may be any value between about 0.05 inches (1.27 mm) and about 0.5 inches (12.7 mm). Additionally, although all of ribs 232 are depicted as extending distally away from base portion 234 the same distance, in other embodiments, each of ribs 232 may extend distally away from base portion 234 different distances, or groups of one or more ribs 232 may extend distally away from base portion 234 different distances. In at least some embodiments where ribs 232 extend helically around longitudinal axis 237, ribs 232 may extend away from base portion 234 a is distance such that at least two separate ribs cross longitudinal axis 237. In other of these embodiments, at least three separate ribs may cross longitudinal axis 237. In still other embodiments, based on the distance 238 ribs 232 extend distally away from base portion 234, every one of ribs 232 may cross longitudinal axis 237.

In some embodiments, collar member 242 may include channels 236 defined by distally extending portion 235. For instance, collar member 242 may be made from a hollow tube. The hollow tube may be machined, laser cut, or otherwise processed (for instance, as explored more fully below) to remove material to define channels 236 extending along longitudinal axis 237 for at least a portion of collar member 242. Channels 236 may be angled with respect to longitudinal axis 237 at an angle similar to how ribs 232 may be angled with respect to base portion 234. For instance, channels 236 may be angled with respect to longitudinal axis 237 between about 15 degrees and about 75 degrees, between about 30 degrees and about 60 degrees, or about 45 degrees. In the embodiments shown in FIGS. 5A and 5B, channels 236 may have one closed end, for instance where each channel 236 meets base portion 234, and one open end, for instance at distal end 223. Additionally, different embodiments of collar member 242 may include varying numbers of channels 236, for instance any number between about two and ten channels, or between about four channels and seven channels.

As illustrated in FIG. 5B, in some embodiments, collar member 242 may additionally include angled extension 239. Angled extension 239 may extend distally away from base portion 234 in a similar manner to ribs 232. However, angled extension 239 may extend in a direction generally transverse to ribs 232. For example, as ribs 232 are depicted extending helically in a clock-wise manner, angled extension 239 may extend in a generally counter-clockwise manner. As depicted in FIG. 5B, angled extension 239 may form an angle $\beta$ with line 230, which represents an extension of the distal-most edge of base portion 234. In the example of FIG. 5B, angle $\beta$ represents an angle of 45 degrees. However, in different embodiments, angle $\beta$ may have any value between about 15 degrees and 75 degrees. In more specific embodiments, angle $\beta$ may have any value between about 30 degrees and 60 degrees. In some embodiments, angle $\beta$ may have the same value as angle $\alpha$, but this does not need to be true in all embodiments. Further, in at least some embodiments, one or more of ribs 232 may extend from angled extension 239, as depicted in FIG. 5B, but this does not need to be the case in all embodiments.

Figure 6A:
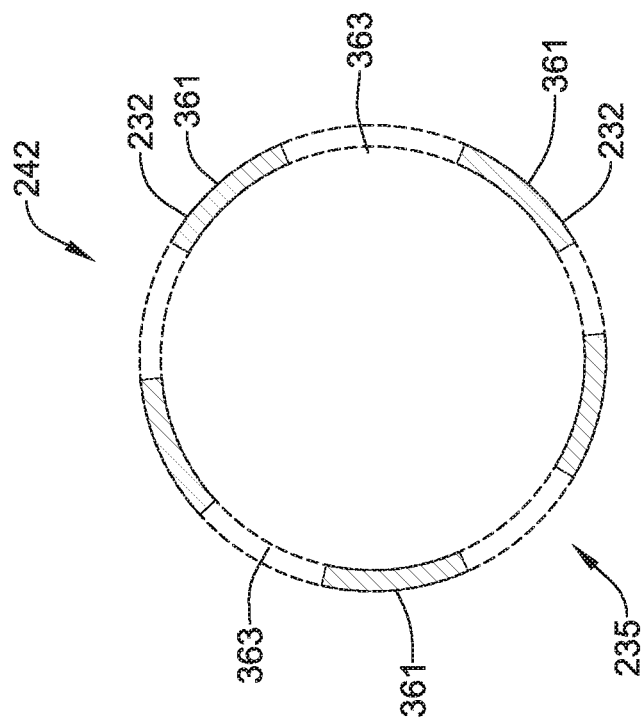
FIG. 6A is a schematic cross-sectional view of the guide extension catheter collar of FIGS. 5A and 5B taken along line A-A.
Figure 6B:
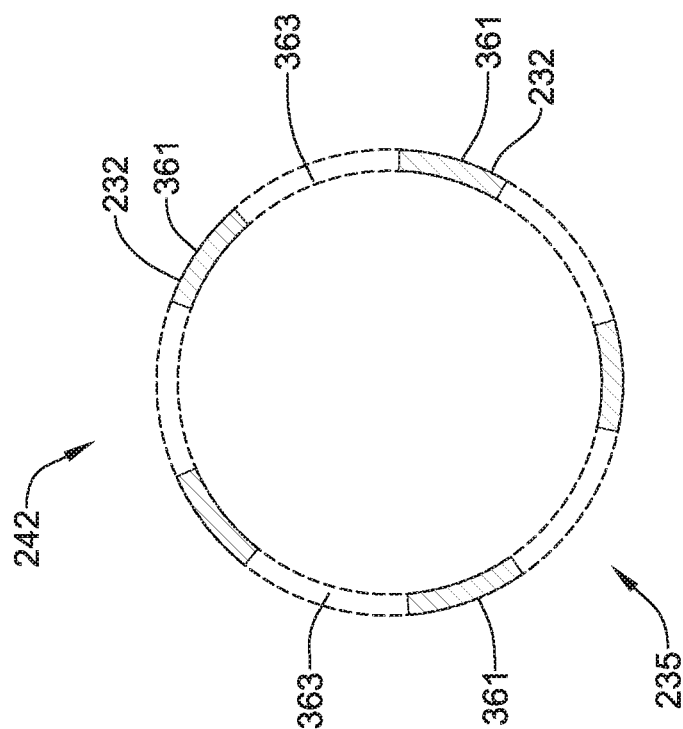
FIG. 6B is a schematic cross-sectional view of the guide extension catheter collar of FIGS. 5A and 5B taken along line B-B.

Another way to define features of collar member 242 is depicted through FIGS. 6A and 6B. FIG. 6A depicts a cross-sectional slice of collar member 242 taken along line A-A transverse to the longitudinal direction of collar member 242, as depicted in FIG. 5A. FIG. 6A shows the total cross-sectional surface area of collar member 242 in a plane defined along line A-A. The total cross-sectional surface area is the sum of all of shaded sections 361, which represent the cross-sectional areas of ribs 232 taken along line A-A. FIG. 6B depicts a slice of collar member 242 taken along line B-B transverse to the longitudinal direction of collar member 242, as depicted in FIG. 5A. FIG. 6B shows the total cross-sectional surface area of collar member 242 in a plane defined along line B-B. Again, the total cross-sectional surface area is the sum of all of shaded sections 361, which represent the cross-sectional areas of ribs 232.

As can be seen in cross-section in FIGS. 6A and 6B, ribs 232 are interspersed with open spaces 363. In FIG. 6A, these open spaces 363 are larger than cross-sectional areas 361. This is in contrast to FIG. 6B, where cross-sectional areas 361 are larger and are more equal in size with the open areas 363. Accordingly, collar member 242 may have differing cross-sectional areas depending on the position of the cross-section along distally extending portion 235. In some embodiments, collar member 242 may have a cross-sectional surface area that does not vary more than 30% throughout distally extending portion 235. For instance, the portion of the distally extending portion 235 with the greatest cross-sectional surface area and the portion of the distally extending portion 235 with the least cross-sectional surface area may have values within about 40% of each other. In other embodiments, distally extending portion 235 may have a cross-sectional surface area that does not vary more than 40% throughout distally extending portion 235, or 33%, 20%, or 10% in still other embodiments. In still other embodiments, the specific amounts by which the cross-sectional surface area of distally extending portion 235 varies throughout distally extending portion 235 may be greater or less than these specific disclosed percentages. In alternative embodiments, distally extending portion 235 may have a similar amount, or the same amount, of cross-sectional surface area throughout distally extending portion 235 such that, at any cross-section defined along a line through distally extending portion 235, the cross-sectional area of distally extending portion is the same or similar. In still other embodiments, the cross-sectional surface area of distally extending portion 235 may taper from where distally extending portion 235 connects to base portion 234 to distal end 223. In at least some of these embodiments, the cross-sectional surface area of distally extending portion 235 where distally extending portion 235 connects to base portion 234 is not more than 40% larger than the cross-sectional surface area of distally extending portion 235 at distal end 223. In other embodiments, the percentage difference may be no more than 33%, 20%, or 10% in other embodiments. In still other embodiments, the specific amounts by which the cross-sectional surface area of distally extending portion 235 tapers may be greater or less than these specific disclosed percentages.

Another way to describe the cross-sections of FIGS. 6A and 6B may be to relate the cross-sectional surface areas of distally extending portion 235 and open spaces 363. For instance, in FIG. 6A, the ratio of the total cross-sectional surface area of distally extending portion 235, as indicated by the cross-sectional surface areas 361, and the total cross-sectional surface area of open spaces 363 may be one to three. In FIG. 6B, the ratio of the total cross-sectional surface area of distally extending portion 235, as indicated by the cross-sectional surface areas 361, and the total cross-sectional surface area of open spaces 363 may be one to one. However, in other embodiments, the ratio of these cross-sectional surface areas may range anywhere from one to four to three to one. Additionally, in at least some embodiments, the ratio may decrease from where distally extending portion 235 connects to base portion 234 all the way to distal end 223 of collar member 242.

The open spaces disposed between portions of collar member 242 may facilitate bonding collar member 242 to distal sheath 26. For instance, when collar member 242 is bonded to distal sheath 26, distally extending portion 235 may be inserted into one end of distal sheath 26 and a portion of distal sheath 26 may be heated to reflow the polymer of distal sheath 26. When heated sufficiently, the polymer may then flow into and/or around distally extending portion 235 and into open spaces 363. When the heating is ceased, the reflowed polymer may harden. Once hardened, the reflowed polymer may form proximally extending portions that extend from distal end 223 of collar member 242 all the way to base portion 234, filling channels 236. In some embodiments, the reflowed polymer may additionally flow over distally extending portion 235 such that a thin layer of the reflowed polymer is disposed on the outer surface of distally extending portion 235. A cross-section of distally extending portion 235 after bonding to distal sheath 26 would reveal cross-sections of distally extending portion 235 interspersed with cross-sections of the reflowed portions of distal sheath 26. Accordingly, the cross-sectional area of the reflowed portions of distal sheath 26 may vary as the cross-sectional area of distally extending portion 235 varies.

The embodiments of collar member 242 disclosed herein may facilitate a strong bond between collar member 242 and distal sheath 26. For instance, the disclosed features of distally extending portion 235 may allow for portions of distal sheath that penetrate throughout distally extending portion 23526 after bonding. Additionally, these penetrating portions may have relatively large cross-sectional areas that maintain integrity of distal sheath 26 throughout distally extending portion 235.

In general, collar member 242 may be made from any suitable method, and may vary depending on the specific material or materials chosen for collar member 242. For example, if collar member 242 is made from a metal or metal alloy, collar member 242 may be formed by photo-etching, laser-cutting, micro-machining, 3D printing, sintering, rolled from flat sheet-stock. However, if collar member 242 is made from a polymer material, collar member 242 may be made through extrusion.

The materials that can be used for the various components of the guide extension catheters disclosed herein may vary. For simplicity purposes, the following discussion makes reference to proximal member 16, distal sheath 26, and collar member 242. However, this is not intended to limit the devices and methods described herein, as the discussion may be applied to other similar tubular members and collars and/or components of tubular members or collars or other devices disclosed herein.

Proximal member 16, distal sheath 26, collar member 242 and/or other components of guide extension catheter 14 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304 L, and 316 LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal is analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of proximal member 16, distal sheath 26, and/or collar member 242 may also be loaded with, made of, or otherwise include a radiopaque material. Radiopaque materials are understood to be materials capable of producing a relatively bright image on a fluoroscopy screen or another imaging technique during a medical procedure. This relatively bright image aids the user of guide extension catheter 14 in determining its location. Some examples of radiopaque materials can include, but are not limited to, gold, platinum, palladium, tantalum, tungsten alloy, polymer material loaded with a radiopaque filler (e.g., barium sulfate, bismuth subcarbonate, etc.), and the like. Additionally, other radiopaque marker bands and/or coils may also be incorporated into the design of guide extension catheter 14 to achieve the same result.

In some embodiments, a degree of Magnetic Resonance Imaging (MRI) compatibility is imparted into guide extension catheter 14. For example, proximal member 16, distal sheath 26, and collar member 242, or portions thereof, may be made of a material that does not substantially distort the image and create substantial artifacts (i.e., gaps in the image). Certain ferromagnetic materials, for example, may not be suitable because they may create artifacts in an MRI image. Proximal member 16, distal sheath 26, and collar member 242, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In at least some embodiments, a sheath or covering (not shown) may be disposed over portions or all of proximal member 16 and distal sheath 26 that may define a generally smooth outer surface for guide extension catheter 14. In other embodiments, however, such a sheath or covering may be absent from a portion of all of guide extension catheter 14, such that proximal member 16 and distal sheath 26 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for is example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guide extension catheter 14 (including, for example, the exterior surface of proximal member 16 and distal sheath 26) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of proximal member 16 and distal sheath 26, or other portions of guide extension catheter 14. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

What is claimed is:

1. A guide extension catheter comprising:
a proximal member having a proximal end, a distal end, a proximal diameter, and a first central axis;
a collar member having a proximal end and a distal end at opposing ends of the collar member, the proximal end of the collar member attached to the distal end of the proximal member and the collar member comprising a base portion and plurality of ribs connected to the base portion and extending from and distally away from the base portion and defining the distal end of the collar member;
a distal sheath member attached to the collar member, the distal sheath member having a distal diameter larger than the proximal diameter and a second central axis that is offset from the first central axis; and
wherein the base portion includes a cross-sectional dimension greater than the proximal diameter.

2. The guide extension catheter of claim 1, wherein each of the plurality of ribs are connected to the base portion at an angle extending from a respective rib of the plurality of ribs to a top of the base portion of between 15 degrees and 75 degrees.

3. The guide extension catheter of claim 1, wherein each of the plurality of ribs are connected to the base portion at an angle extending from a respective rib of the plurality of ribs to a top of the base portion of between 30 degrees and 60 degrees.

4. The guide extension catheter of claim 1, wherein each of the plurality of ribs are connected to the base portion at an angle extending from a respective rib of the plurality of ribs to a top of the base portion of 45 degrees.

5. The guide extension catheter of claim 1, wherein the plurality of ribs comprise between two ribs and ten ribs.

6. The guide extension catheter of claim 1, wherein the plurality of ribs comprise five ribs.

7. The guide extension catheter of claim 1, wherein the plurality of ribs extend away from the base portion in a twisting manner.

8. The guide extension catheter of claim 1, wherein the plurality of ribs extend away from the base portion in a helical manner.

9. The guide extension catheter of claim 1, wherein each of the plurality of ribs extends away from the base portion a same distance.

10. A guide extension catheter comprising:
a proximal member having a proximal end, a distal end, a proximal diameter, and a first central axis;
a hollow tube extending along a longitudinal axis and attached to the distal end of the proximal member, the hollow tube defining one or more channels extending along at least a portion of the hollow tube; and
a distal sheath member attached to the hollow tube, the distal sheath member having a distal diameter greater than the proximal diameter and a second central axis that is offset from the first central axis,
wherein the channels are angled with respect to the longitudinal axis of the hollow tube.

11. The guide extension catheter of claim 10, wherein the one or more channels are angled between about 15 degrees and 75 degrees with respect to the longitudinal axis.

12. The guide extension catheter of claim 10, wherein the one or more channels are angled between about 30 degrees and 60 degrees with respect to the longitudinal axis.

13. The guide extension catheter of claim 10, wherein the one or more channels comprise between two channels and ten channels.

14. The guide extension catheter of claim 10, wherein the one or more channels comprise between four and seven channels.

15. The guide extension catheter of claim 10, wherein the hollow tube defines the one or more channels such that each of the one or more channels has an open end and a closed end.

16. A guide extension catheter comprising:
a proximal member having a proximal end, a distal end, a proximal diameter, and a first central axis;
a collar member attached to the proximal member, the collar member having a proximal end and distal end and comprising a base portion and a distally extending portion; and
a distal sheath member attached to the collar member, the distal sheath member having a distal diameter greater than the proximal diameter and a second central axis that is offset from the first central axis,
wherein the distally extending portion has a cross-sectional surface area that varies less than 33% through the distally extending portion.

17. The guide extension catheter of claim 16, wherein the collar member has a cross-sectional surface area that varies less than 10% along the distally extending portion.

18. The guide extension catheter of claim 16, wherein the distally extending portion comprises ribs connected to the base portion and extending distally away from the base portion.

19. The guide extension catheter of claim 18, wherein the ribs extend distally away from the base portion in a helically twisting manner.

20. The guide extension catheter of claim 1, wherein the plurality of ribs extend away from the base portion in a helical manner and terminate at a distal free end adjacent the distal end of the collar member.

* * * * *